United States Patent
Nakayama et al.

(10) Patent No.: US 7,198,932 B1
(45) Date of Patent: Apr. 3, 2007

(54) GDP-4-KETO-6-DEOXY-D-MANNOSE-3,5-EPIMERASE-4-REDUCTASE GENE DERIVED FROM ARABIDOPSIS THALIANA

(75) Inventors: Ken-ichi Nakayama, Ibaraki (JP); Yoshifumi Jigami, Ibaraki (JP)

(73) Assignee: National Institute of Advanced Industrial Science and Technology, Tokyo (JP)

(*) Notice: Subject to any disclaimer, the term of this patent is extended or adjusted under 35 U.S.C. 154(b) by 0 days.

(21) Appl. No.: 10/089,014

(22) PCT Filed: Mar. 30, 2000

(86) PCT No.: PCT/JP00/02049

§ 371 (c)(1), (2), (4) Date: Mar. 25, 2002

(87) PCT Pub. No.: WO01/38507

PCT Pub. Date: May 31, 2001

(30) Foreign Application Priority Data

Nov. 19, 1999 (JP) ................................ 11-329045

(51) Int. Cl.
*C12N 9/90* (2006.01)
*C12N 9/00* (2006.01)
*C12P 1/00* (2006.01)
*C12P 21/06* (2006.01)

(52) U.S. Cl. ............................... 435/233; 435/4; 435/6; 435/41; 435/69.1; 435/183; 435/189; 435/252.3; 435/320.1; 536/23.2; 536/23.3; 536/23.4; 530/350

(58) Field of Classification Search .............. 435/69.1, 435/183, 189, 190, 233, 252.3, 320.1, 41, 435/72, 94, 4, 325, 6, 252.2; 536/23.2–23.7; 530/350
See application file for complete search history.

(56) References Cited

FOREIGN PATENT DOCUMENTS

| EP | 0 870 841 A | 10/1998 |
|---|---|---|
| WO | WO 99 36555 A | 7/1999 |
| WO | WO 99/64618 | 12/1999 |

OTHER PUBLICATIONS

Andrianopoulos et al. 1998 (J. Bacteriol., vol. 180(4):998-1001).*
Bonin et al. 1997 (Plant Physiol., vol. 114(3), Sup. p. 22, Abstract 20.*

(Continued)

*Primary Examiner*—Manjunath Rao
(74) *Attorney, Agent, or Firm*—Fish & Richardson P.C.

(57) ABSTRACT

The present invention relates to a gene for an enzyme involving in the synthesis of GDP-L-fucose. Particularly, the present invention relates to a GDP-4-keto-6-deoxy-D-mannose-3, 5-epimerase-4-reductase gene derived from *Arabidopsis thaliana*, and a process for producing GDP-L-fucose using the gene. An enzyme encoded by the gene is (a) a protein comprising an amino acid sequence represented by SEQ ID NO: 1; or (b) a protein comprising an amino acid sequence derived from the amino acid sequence of SEQ ID NO: 1 by deletion, substitution, addition or insertion of one or several amino acid residues, and having GDP-4-keto-6-deoxy-D-mannose-3, 5-epimerase-4-reductase activity. The present invention enables efficient mass production of GDP-L-fucose which is essential in performing addition of fucose, which has a very important function in sugar chains.

8 Claims, 3 Drawing Sheets

OTHER PUBLICATIONS

SPTREMBL database accession No. O49213, Jun. 1998, Bonin et al.*

Chang et al. J. Biol. Chem., 1988, vol. 263(4):1693-97.*

M. Tonetti et al, "Preliminary crystallographic investigations of recombinant GDP-4-keto-6-deoxy-d-mannose epimerase/reductase from *E coli*", *International Union of Crystallography*; vol. 54, No. 4, pp. 684-686 (1996).

Abstract—Bonin et al., (1998) "Arabidopsis thaliana GDP-4-keto-6-deoxy-D-mannose-3,5-epimerase-4-reductase (GER1) gene, complete cds." Database accession No. AF045286 XP002176506.

Bonin et al. (1997) "The MUR1 gene of Arabidopsis thaliana encodes an isoform of GDP -D-mannose-4,6-dehydratase, catalyzing the first step in the de novo synthesis of GDP-L-fucose" Proc. Natl. Acad. Sci . USA 94(5):2085-2090.

* cited by examiner

1, 4; strain W303
2 ; strain expressing MUR1 only
5 ; strain expressing AtFX only
3, 6; strain co-expressing MUR1 and AtFX

Fig. 3

1; strain W303

2; strain expressing MUR1 only

3; strain expressing AtFX only

4; strain co-expressing MUR1 and AtFX

SEQUENCE LISTING

<160> NUMBER OF SEQ ID NOS: 6

<210> SEQ ID NO 1
<211> LENGTH: 312
<212> TYPE: PRT
<213> ORGANISM: Arabidopsis thaliana

<400> SEQUENCE: 1

```
Met Ser Asp Lys Ser Ala Lys Ile Phe Val Ala Gly His Arg Gly Leu
 1               5                  10                  15

Val Gly Ser Ala Ile Val Arg Lys Leu Gln Glu Gln Gly Phe Thr Asn
            20                  25                  30

Leu Val Leu Lys Thr His Ala Glu Leu Asp Leu Thr Arg Gln Ala Asp
        35                  40                  45

Val Glu Ser Phe Phe Ser Gln Glu Lys Pro Val Tyr Val Ile Leu Ala
    50                  55                  60

Ala Ala Lys Val Gly Gly Ile His Ala Asn Asn Thr Tyr Pro Ala Asp
65                  70                  75                  80

Phe Ile Gly Val Asn Leu Gln Ile Gln Thr Asn Val Ile His Ser Ala
                85                  90                  95

Tyr Glu His Gly Val Lys Lys Leu Leu Phe Leu Gly Ser Ser Cys Ile
            100                 105                 110

Tyr Pro Lys Phe Ala Pro Gln Pro Ile Pro Glu Ser Ala Leu Leu Thr
        115                 120                 125

Ala Ser Leu Glu Pro Thr Asn Glu Trp Tyr Ala Ile Ala Lys Ile Ala
    130                 135                 140

Gly Ile Lys Thr Cys Gln Ala Tyr Arg Ile Gln His Gly Trp Asp Ala
145                 150                 155                 160

Ile Ser Gly Met Pro Thr Asn Leu Tyr Gly Pro Asn Asp Asn Phe His
                165                 170                 175

Pro Glu Asn Ser His Val Leu Pro Ala Leu Met Arg Arg Phe His Glu
            180                 185                 190

Ala Lys Val Asn Gly Ala Glu Val Val Val Trp Gly Thr Gly Ser
        195                 200                 205

Pro Leu Arg Glu Phe Leu His Val Asp Asp Leu Ala Asp Ala Cys Val
    210                 215                 220

Phe Leu Leu Asp Arg Tyr Ser Gly Leu Glu His Val Asn Ile Gly Ser
225                 230                 235                 240

Gly Gln Glu Val Thr Ile Arg Glu Leu Ala Glu Leu Val Lys Glu Val
                245                 250                 255

Val Gly Phe Glu Gly Lys Leu Gly Trp Asp Cys Thr Lys Pro Asp Gly
            260                 265                 270

Thr Pro Arg Lys Leu Met Asp Ser Ser Lys Leu Ala Ser Leu Gly Trp
        275                 280                 285

Thr Pro Lys Val Ser Leu Arg Asp Gly Leu Ser Gln Thr Tyr Asp Trp
    290                 295                 300

Tyr Leu Lys Asn Val Cys Asn Arg
305                 310
```

<210> SEQ ID NO 2
<211> LENGTH: 936
<212> TYPE: DNA
<213> ORGANISM: Arabidopsis thaliana
<220> FEATURE:
<221> NAME/KEY: CDS

<222> LOCATION: (1)...(936)

<400> SEQUENCE: 2

| | | | | | | | | | | | | | | | | |
|---|---|---|---|---|---|---|---|---|---|---|---|---|---|---|---|---|
| atg | tct | gac | aaa | tct | gcc | aaa | atc | ttc | gtc | gcg | ggt | cat | cgt | ggt | ttg | 48 |
| Met | Ser | Asp | Lys | Ser | Ala | Lys | Ile | Phe | Val | Ala | Gly | His | Arg | Gly | Leu | |
| 1 | | | | 5 | | | | | 10 | | | | | 15 | | |
| gtt | gga | tct | gcc | att | gtc | cgc | aag | ctt | cag | gaa | caa | ggt | ttc | acc | aat | 96 |
| Val | Gly | Ser | Ala | Ile | Val | Arg | Lys | Leu | Gln | Glu | Gln | Gly | Phe | Thr | Asn | |
| | | | 20 | | | | | 25 | | | | | 30 | | | |
| ctc | gtt | ctt | aaa | aca | cac | gcc | gag | ctt | gat | ctc | act | cgt | caa | gcc | gat | 144 |
| Leu | Val | Leu | Lys | Thr | His | Ala | Glu | Leu | Asp | Leu | Thr | Arg | Gln | Ala | Asp | |
| | | 35 | | | | | 40 | | | | | 45 | | | | |
| gtt | gaa | tcc | ttc | ttt | tct | caa | gag | aag | cca | gtt | tat | gta | atc | cta | gca | 192 |
| Val | Glu | Ser | Phe | Phe | Ser | Gln | Glu | Lys | Pro | Val | Tyr | Val | Ile | Leu | Ala | |
| 50 | | | | | 55 | | | | | 60 | | | | | | |
| gca | gct | aaa | gtt | ggt | ggt | att | cac | gct | aac | aac | acc | tat | cct | gct | gat | 240 |
| Ala | Ala | Lys | Val | Gly | Gly | Ile | His | Ala | Asn | Asn | Thr | Tyr | Pro | Ala | Asp | |
| 65 | | | | 70 | | | | | 75 | | | | | 80 | | |
| ttc | att | ggt | gtc | aat | ctc | cag | att | cag | acc | aat | gtg | atc | cac | tct | gca | 288 |
| Phe | Ile | Gly | Val | Asn | Leu | Gln | Ile | Gln | Thr | Asn | Val | Ile | His | Ser | Ala | |
| | | | | 85 | | | | | 90 | | | | | 95 | | |
| tat | gag | cac | ggt | gtg | aag | aag | ctt | ctc | ttc | ctt | gga | tca | tcc | tgc | att | 336 |
| Tyr | Glu | His | Gly | Val | Lys | Lys | Leu | Leu | Phe | Leu | Gly | Ser | Ser | Cys | Ile | |
| | | | 100 | | | | | 105 | | | | | 110 | | | |
| tac | cct | aaa | ttt | gct | cct | cag | cca | att | cct | gag | tct | gct | ttg | tta | aca | 384 |
| Tyr | Pro | Lys | Phe | Ala | Pro | Gln | Pro | Ile | Pro | Glu | Ser | Ala | Leu | Leu | Thr | |
| | | 115 | | | | | 120 | | | | | 125 | | | | |
| gca | tcg | ctt | gaa | cca | act | aat | gag | tgg | tat | gct | att | gct | aag | atc | gct | 432 |
| Ala | Ser | Leu | Glu | Pro | Thr | Asn | Glu | Trp | Tyr | Ala | Ile | Ala | Lys | Ile | Ala | |
| 130 | | | | | 135 | | | | | 140 | | | | | | |
| ggg | att | aag | act | tgt | cag | gct | tat | agg | att | cag | cac | gga | tgg | gat | gca | 480 |
| Gly | Ile | Lys | Thr | Cys | Gln | Ala | Tyr | Arg | Ile | Gln | His | Gly | Trp | Asp | Ala | |
| 145 | | | | 150 | | | | | 155 | | | | | 160 | | |
| atc | tct | ggc | atg | cct | act | aat | ctc | tat | ggt | cct | aat | gac | aat | ttc | cac | 528 |
| Ile | Ser | Gly | Met | Pro | Thr | Asn | Leu | Tyr | Gly | Pro | Asn | Asp | Asn | Phe | His | |
| | | | | 165 | | | | | 170 | | | | | 175 | | |
| ccg | gag | aat | tct | cat | gtg | ctt | cct | gct | ctt | atg | agg | agg | ttc | cac | gag | 576 |
| Pro | Glu | Asn | Ser | His | Val | Leu | Pro | Ala | Leu | Met | Arg | Arg | Phe | His | Glu | |
| | | | 180 | | | | | 185 | | | | | 190 | | | |
| gcg | aaa | gtg | aat | gga | gcg | gag | gaa | gtt | gtg | gtg | tgg | ggt | aca | ggt | agt | 624 |
| Ala | Lys | Val | Asn | Gly | Ala | Glu | Glu | Val | Val | Val | Trp | Gly | Thr | Gly | Ser | |
| | | 195 | | | | | 200 | | | | | 205 | | | | |
| ccg | ttg | agg | gag | ttc | ttg | cat | gtt | gat | gat | ttg | gct | gat | gct | tgt | gtt | 672 |
| Pro | Leu | Arg | Glu | Phe | Leu | His | Val | Asp | Asp | Leu | Ala | Asp | Ala | Cys | Val | |
| 210 | | | | | 215 | | | | | 220 | | | | | | |
| ttc | ttg | ctg | gat | cga | tac | agc | ggg | ttg | gag | cat | gtt | aac | att | gga | agt | 720 |
| Phe | Leu | Leu | Asp | Arg | Tyr | Ser | Gly | Leu | Glu | His | Val | Asn | Ile | Gly | Ser | |
| 225 | | | | 230 | | | | | 235 | | | | | 240 | | |
| ggt | caa | gaa | gtg | act | att | aga | gag | ttg | gct | gag | ttg | gtg | aaa | gag | gtt | 768 |
| Gly | Gln | Glu | Val | Thr | Ile | Arg | Glu | Leu | Ala | Glu | Leu | Val | Lys | Glu | Val | |
| | | | | 245 | | | | | 250 | | | | | 255 | | |
| gtt | ggt | ttt | gaa | ggg | aag | ctt | gga | tgg | gat | tgc | act | aag | cca | gat | ggc | 816 |
| Val | Gly | Phe | Glu | Gly | Lys | Leu | Gly | Trp | Asp | Cys | Thr | Lys | Pro | Asp | Gly | |
| | | | 260 | | | | | 265 | | | | | 270 | | | |
| aca | ccg | agg | aaa | ctt | atg | gac | agc | tca | aag | ctc | gcg | tct | ttg | ggt | tgg | 864 |
| Thr | Pro | Arg | Lys | Leu | Met | Asp | Ser | Ser | Lys | Leu | Ala | Ser | Leu | Gly | Trp | |
| | | 275 | | | | | 280 | | | | | 285 | | | | |
| aca | cct | aag | gtt | tct | ctt | aga | gat | ggt | ctg | agc | caa | act | tat | gat | tgg | 912 |
| Thr | Pro | Lys | Val | Ser | Leu | Arg | Asp | Gly | Leu | Ser | Gln | Thr | Tyr | Asp | Trp | |
| | | 290 | | | | | 295 | | | | | 300 | | | | |

```
tat ttg aag aat gtt tgc aac cga                                   936
Tyr Leu Lys Asn Val Cys Asn Arg
305                 310

<210> SEQ ID NO 3
<211> LENGTH: 39
<212> TYPE: DNA
<213> ORGANISM: Artificial Sequence
<220> FEATURE:
<223> OTHER INFORMATION: primer

<400> SEQUENCE: 3
attggtacca tgtctgacaa atctgccaaa atcttcgtc                         39

<210> SEQ ID NO 4
<211> LENGTH: 50
<212> TYPE: DNA
<213> ORGANISM: Artificial Sequence
<220> FEATURE:
<223> OTHER INFORMATION: primer

<400> SEQUENCE: 4
ttagtcgacg atatctcggt tgcaaacatt cttcaaatac caatcataag             50

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
gtcgaattca tggcgtcaga gaacaac                                      27

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
gaactcgaga ggttgctgct tagcatc                                      27
```

GDP-4-KETO-6-DEOXY-D-MANNOSE-3,5-EPIMERASE-4-REDUCTASE GENE DERIVED FROM ARABIDOPSIS THALIANA

TECHNICAL FIELD

The present invention relates to a gene of an enzyme involving in the synthesis of GDP-L-fucose. In particular, the present invention relates to a GDP-4-keto-6-deoxy-D-mannose-3, 5-epimerase-4-reductase gene derived from *Arabidopsis thaliana*, and a process for producing GDP-L-fucose using this gene.

BACKGROUND ART

The sugar chain of glycoprotein or the like is known to play a very important role in vivo. Thus, sugar chain engineering, by which the sugar chain structure is intendedly altered, is now an essential technical field. Current techniques for altering sugar chains include, for example, a chemical technique which binds chemically-synthesized target sugar chains to a protein; a biological technique which alters genes for the synthesis of a sugar-chain within a cell by a genetic engineering technique, or produces glycoprotein by altering a host which produces glycoprotein; and a method of sugar-chain synthesis which uses sugar-chain synthetic enzymes.

Progress in the chemical technique is now opening up a way for mass synthesis, however, it is not yet able to easily provide all the types of sugar chains owing to the complexity of sugar chains. On the other hand, thanks to the development of genetic engineering, in the biological technique, control of the expression of genes involving in sugar-chain synthesis is now available, enabling alteration of sugar chains. However, uniform synthesis of all the types of sugar chains is currently difficult, and usually a mixture of different types of sugar chains exists within the product.

In contrast to these techniques, in vitro sugar-chain synthesis using sugar-chain synthetic enzymes is very useful in the synthesis of sugar-chains with a uniform structure. In particular, the combination of such a technique and the biological technique enables mass production of uniform sugar chains.

However, while in vitro sugar-chain synthesis requires the use of sugar nucleotides as sugar donors for glycosyltransferase, the prohibitively high cost of producing sugar nucleotides makes it difficult to apply the method to mass production. That is, sugar nucleotides are present in a very small amount in vivo, and are very reactive, unstable substance which are linked by a high-energy bond. Therefore, only a small amount of sugar nucleotides is produced in each organism, and mass production thereof is difficult.

In recent years, a production system using bacteria has enabled a more practical mass production system of relatively many types of sugar nucleotides, and has enabled a more stable supply of sugar nucleotides. However, a production system with a relatively long reaction process results in low yield, since the system comprises the steps of mixing two types of microorganisms and performing the production using disrupted cells in order to introduce a material contained in cells into other cells. Thus, development of a new technique is being sought.

Figure 1:
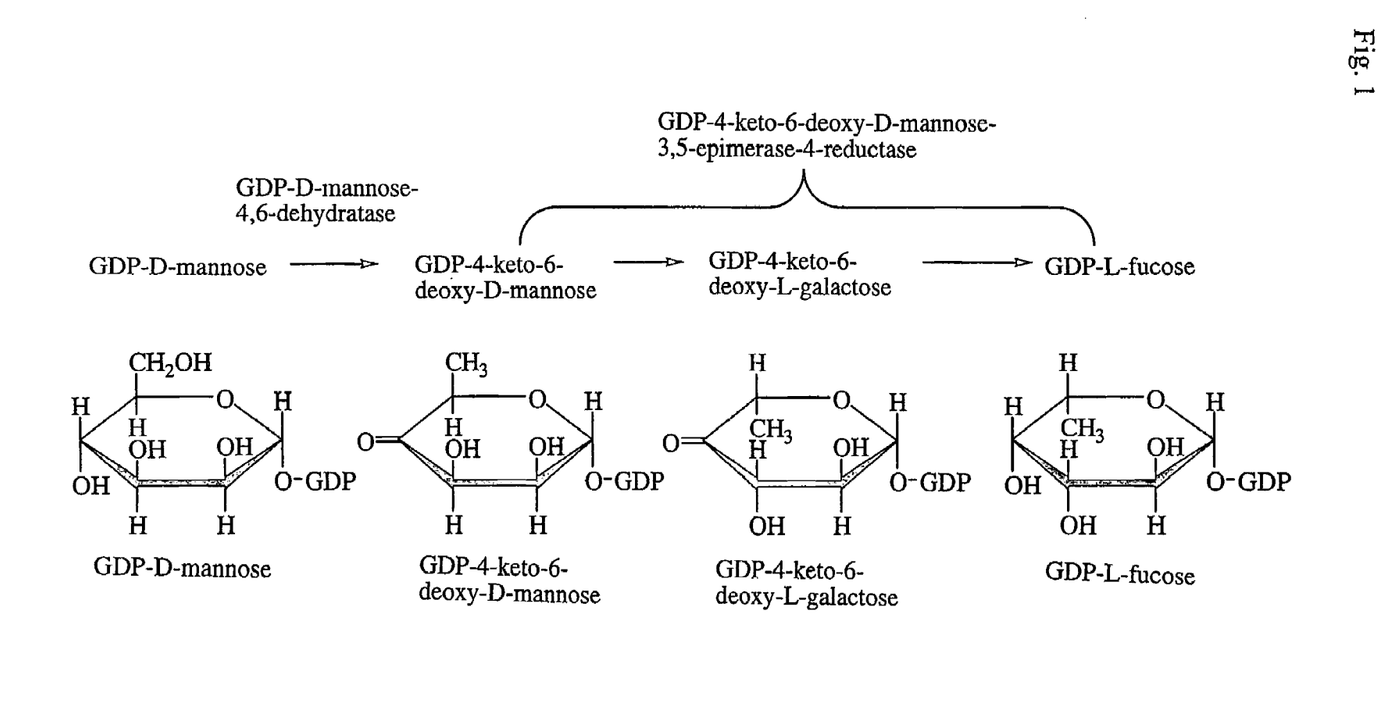
FIG. 1 shows an enzyme reaction process from GDP-D-mannose to GDP-L-fucose.

Among sugar nucleotides, GDP-L-fucose is essential as a sugar donor of fucosyl-transferase for synthesis of sugar chains containing fucose. Sugar chains with the fucose moiety added thereto often play a functionally important role, and therefore providing the sugar donor in large quantities at low cost has been awaited. It has been reported that the GDP-L-fucose is synthesized through 3 reaction steps from GDP-D-mannose, and these 3 reaction steps are catalyzed by two types of enzymes (FIG. 1) (Tonetti et al., J. Biol. Chem., Vol. 271, 27274 (1996)). These enzymes are generally distributed among any organism utilizing fucose, including prokaryotes, such as *Escherichia coli*, and also eukaryotes, such as higher mammals, for example humans. However, these organisms consume the synthesized GDP-L-fucose, so that GDP-L-fucose does not accumulate within their cells. Accordingly, isolation of GDP-L-fucose from a living organism results in a very small amount of GDP-L-fucose at a high cost. Moreover, synthesis of GDP-L-fucose also requires a long process. Under such present circumstances, it is difficult to supply a sufficient amount of GDP-L-fucose using the above bacterial system.

Two types of the enzymes which catalyze the 3 reaction steps are GDP-D-mannose-4, 6-dehydratase, which catalyzes the first reaction step to convert from GDP-D-mannose to GDP-4-keto-6-deoxy-D-mannose by dehydration reaction; and GDP-4-keto-6-deoxy-D-mannose-3, 5-epimerase-4-reductase which catalyses the subsequent two reaction steps, epimerization and reduction. For the plant *Arabidopsis* (*Arabidopsis thaliana*), MUR1 has already been isolated as a gene for GDP-D-mannose-4, 6-dehydratase which catalyzes the first reaction (Bonin et al., Proc. Natl. Acad. Sci. USA, Vol. 94, 2085 (1997)).

However, isolation of a gene for GDP-4-keto-6-deoxy-D-mannose-3, 5-epimerase-4-reductase which catalyzes the subsequent reactions has not been reported. Only a sequence having a high homology with that of the genes for GDP-4-keto-6-deoxy-D-mannose-3, 5-epimerase-4-reductase from another biological species has been submitted to a gene database.

SUMMARY OF THE INVENTION

The present invention is intended to provide a GDP-4-keto-6-deoxy-D-mannose-3, 5-epimerase-4-reductase gene for efficiently synthesizing GDP-L-fucose.

As a result of thorough studies to solve the above problems, we have isolated a gene (AtFX gene) which encodes GDP-4-keto-6-deoxy-D-mannose-3, 5-epimerase-4-reductase derived from *Arabidopsis* (*Arabidopsis thaliana*) which catalyzes the latter two reaction steps in the synthesis of GDP-L-fucose from GDP-D-mannose and determined the nucleotide sequence of the gene, and thereby we have reached the present invention by finding that GDP-L-fucose can be efficiently synthesized in vivo and in vitro by co-expression of the gene and MUR1 gene which catalyzes the first reaction in the synthesis of GDP-L-fucose in *Arabidopsis*.

Specifically, the present invention provides the protein of the following (a) or (b):

(a) a protein comprising an amino acid sequence represented by SEQ ID NO: 1;

(b) a protein comprising an amino acid sequence derived from the amino acid sequence of SEQ ID NO: 1 by deletion, substitution, addition or insertion of one or several amino acid residues, and having GDP-4-keto-6-deoxy-D-mannose-3, 5-epimerase-4-reductase activity.

Further, the present invention provides DNA encoding the protein of the following (a) or (b):

(a) a protein comprising an amino acid sequence represented by SEQ ID NO: 1;

(b) a protein comprising an amino acid sequence derived from the amino acid sequence of SEQ ID NO: 1 by deletion, substitution, addition or insertion of one or several amino acid residues, and having GDP-4-keto-6-deoxy-D-mannose-3, 5-epimerase-4-reductase activity.

The DNA preferably comprises a nucleotide sequence represented by SEQ ID NO: 2.

The present invention further provides an expression vector which comprises the DNA.

The present invention further provides a transformant which is transformed with the expression vector. An example of such a transformant is yeast strain W303/pYO-AtFX-Myc (FERM BP-7109). Furthermore, the present invention provides a process for producing GDP-4-keto-6-deoxy-D-mannose-3, 5-epimerase-4-reductase, which comprises culturing the transformant according to the invention in a medium, and collecting GDP-4-keto-6-deoxy-D-mannose-3, 5-epimerase-4-reductase from the obtained culture.

The present invention further provides a transformant which is transformed with the expression vector and an expression vector containing DNA encoding GDP-D-mannose-4, 6-dehydratase. An example of such a transformant is yeast strain W303/YEp-MUR1-HA, pYO-AtFx-Myc (FERM BP-7108). Furthermore, the present invention provides a process for converting GDP-D-mannose into GDP-L-fucose using the transformant according to the invention, and a process for producing GDP-L-fucose which comprises culturing the transformant according to the invention together with GDP-D-mannose in a medium, and collecting GDP-L-fucose from the obtained culture.

This specification includes part or all of the contents as disclosed in the specification and/or drawings of Japanese Patent Application No. 11-329045, of which the present application claims the priority.

EXPLANATION OF SEQUENCE LISTING

SEQ ID NOS: 3 to 6: primer

BEST MODE FOR CARRYING OUT THE INVENTION

The present invention will now be described in detail.

In the present specification, abbreviated notations of amino acid sequences and nucleotide sequences are indicated with codes following the regulation of IUPAC-IUB and common names or usage in the technical field.

1. Isolation of a Gene for GDP-4-Keto-6-Deoxy-D-Mannose-3, 5-Epimerase-4-Reductase The gene for GDP-4-keto-6-deoxy-D-mannose-3, 5-epimerase-4-reductase according to the present invention can be isolated by the PCR method using a cDNA library prepared from Arabidopsis (Arabidopsis thaliana) as a template according to standard techniques.

The cDNA library of Arabidopsis thaliana can be produced according to methods known by persons skilled in the art using generally employed plasmid vectors, λ phage-derived vectors or the like. Further, a commercially available cDNA library derived from Arabidopsis thaliana may also be used.

The PCR method is a technique by which a certain region of DNA can be specifically amplified in vitro 10- to a million-fold within about 2 to 3 hours using a combination of the sense primer and the antisense primer, a thermostable DNA polymerase, a DNA amplification system and the like. The DNA according to the present invention can be amplified by the PCR method using appropriate primers.

Primers that can be used in the above PCR can be designed based on, for example, nucleotide sequence homology with other types of enzyme genes. Nucleotide sequences of other types of enzyme genes that can be used herein are those submitted to a known DNA sequence database, such as GenBank, that persons skilled in the art can easily search. Examples of such nucleotide sequences include those submitted to GenBank with accession Nos. U38473, U58766, and AF045286. When designing a primer, a sequence of, for example, a restriction enzyme site, may be contained in the nucleotide sequence of the primer, after considering genetic manipulation to be performed after PCR amplification.

An example of primers which are designed as described above includes those comprising the following nucleotide sequences.

Forward primer:

5'-ATT<u>GGTACC</u>ATGTCTGACAAATCTGCCAAAATCT TCGTC-3'

(SEQ ID NO: 3)

Reverse primer:

5'-TTAGTCGAC<u>GATATC</u>TCGGTTGCAAACATTCTTC AAATACCAATCATAAG-3'

(SEQ ID NO: 4)

The underlined portion in the nucleotide sequence of the forward primer denotes KpnI site, and that in the nucleotide sequence of the reverse primer denotes EcoRV site. The DNA according to the present invention can be amplified well by PCR using these primers.

In addition to a cDNA library to be used as a template and primers, the PCR solution to perform PCR should be supplemented with thermostable DNA polymerase, dNTPs mixture and the like. Such a PCR solution can be appropriately prepared by persons skilled in the art. For example, a PCR solution may be prepared to have the composition shown in the following Table 1.

TABLE 1

| Composition of PCR solution | |
|---|---|
| 10 × LA PCR Buffer II (Mg$^{2+}$ plus) | 5 μl |
| dNTPs Mixture (2.5 mM each) | 8 μl |
| Forward primer (20 pmol/μl) | 1 μl |
| Reverse primer (20 pmol/μl) | 1 μl |
| cDNA library (1 ng/μl) | 1 μl |
| TaKaRa LA Taq (5 U/μl) | 0.5 μl |
| Water | 33.5 μl |
| Total | 50.0 μl |

The PCR conditions may be appropriately determined by persons skilled in the art according to the nucleotide sequences of primers to be used or the like. For example, PCR reaction may be performed by 30 cycles of a reaction cycle consisting of denaturation at 94° C. for 15 sec, annealing at 50° C. for 30 sec, and elongation at 68° C. for 2 min. Such a reaction can be easily performed using a commercially available thermal cycler or the like.

DNA amplified by the above PCR can be cloned into an appropriate plasmid. Any plasmid can be used to incorporate DNA, so far as it can be replicated and maintained in a host. For example, pBR322, pUC19 or the like derived from *Escherichia coli* can be used.

Further, cloning of amplified DNA can also be performed using a commercially available kit. An example of such a kit is TA cloning kit (Invitrogen). When a commercially available kit is used, plasmids contained in the kit can be used.

Examples of a method for incorporating a plasmid containing the DNA according to the present invention into a host, such as *Escherichia coli* include a method described by T. Maniatis et al. [Molecular Cloning, Cold Spring Harbor Laboratory, 1st Edition, p. 250 (1982)], a method described by F. M. Ausubel et al., [Short Protocols in Molecular Biology, 4th Edition, 1–27 (1999)] and the like.

The nucleotide sequence of the DNA according to the present invention can be determined by a known method, such as a dideoxy method, using the plasmids obtained as described above. Such sequencing can be performed using a commercially available kit. An example of such a kit is a Sequence Kit (PE Biosystems). Once determined the nucleotide sequence of the DNA according to the present invention, an deduced amino acid sequence of the protein according to the present invention can be obtained.

The protein according to the present invention comprises an amino acid sequence represented by SEQ ID NO: 1. The protein has GDP-4-keto-6-deoxy-D-mannose-3, 5-epimerase-4-reductase activity. Moreover, the amino acid sequence of the protein according to the present invention is not limited to the sequence of SEQ ID NO: 1. The protein may also comprise an amino acid sequence derived from that of SEQ ID NO: 1 by substitution, deletion, addition or insertion of one or several amino acid residues, so far as the protein maintains GDP-4-keto-6-deoxy-D-mannose-3, 5-epimerase-4-reductase activity.

The DNA according to the present invention comprises a nucleotide sequence encoding an amino acid sequence of the protein according to the present invention as described above. Many nucleotide sequences can be contemplated as such a nucleotide sequence, because multiple coding sequences can exit for one amino acid. An example is a nucleotide sequence represented by SEQ ID NO: 2. The DNA according to the present invention which comprises a nucleotide sequence other than the nucleotide sequence of SEQ ID NO: 2 can be easily prepared by persons skilled in the art, for example by a site-directed mutagenesis (Zoller et al, Nucleic Acids Res., Vol. 10, No. 20, 6487–6500 (1982)), a chemical synthesis method.

2. Construction of an Expression Vector for Expressing the DNA According to the Present Invention An expression vector can be constructed by ligating the cloned DNA according to the present invention downstream of a promoter within a vector appropriate for expression of the DNA. Examples of a vector include plasmids derived from yeast, such as YEp352GAP, YEp51, pSH19, and pYO325, and the like.

The DNA to be used for incorporation into an expression vector is the DNA according to the present invention, and having the translation initiation codon, ATG, at its 5' end and the termination codon, TAA, TGA or TAG at its 3' end.

Further, for example, a gene for labeled antigen, which is a part of hemagglutinin protein, or the gene for a labeled protein, such as GST protein, may be bound at the 5' or 3' end for expression.

To express the gene, a promoter is preferably ligated upstream of the gene. Any promoter can be used according to the present invention, so far as it is an appropriate promoter compatible to a host to be used for gene expression. When a host to be transformed is yeast, examples of a promoter include, for example EN01 promoter, GAL10 promoter, GAPDH promoter and ADH promoter.

A terminator may be ligated downstream of the gene to terminate transcription of the gene. Any terminator can be used according to the present invention, so far as it is an appropriate terminator corresponding to a host to be used for gene expression. When a host to be transformed is yeast, examples of a terminator include, for example EN01 terminator, GAL10 terminator, GAPDH terminator and ADH terminator.

Incorporation of the DNA according to the present invention, a promoter, a terminator and the like into an expression vector can be appropriately performed by persons skilled in the art.

3. Preparation of a Transformant Containing the Expression Vector According to the Present Invention.

A transformant which expresses the protein according to the present invention can be prepared by introducing into an appropriate host the expression vector according to the present invention which is constructed as described in the above "2. Construction of an expression vector for expressing the DNA according to the present invention."

Any host can be used, so far as it does not consume GDP-L fucose in vivo. Such a host is not specifically limited, and preferably, yeast is used. Examples of yeast include budding yeast (*Saccharomyces cerevisiae*) and other yeast (*Pichia pastoris* and the like). When yeast extracts are used for producing GDP-L-fucose, that is when GDP-L-fucose is produced in vitro, any host can be used, so far as it enables expression of the protein according to the present invention within the cytoplasm.

The above transformant can be produced by a method generally employed for each host. For example, when a host is yeast, the expression vector according to the present invention is introduced by a lithium method, electroporation method or the like.

The obtained transformant is, for example, strain W303/pYO-AtFX-Myc (FERM BP-7109).

To produce GDP-L-fucose by culturing the transformants, hosts are required to be previously transformed with expression vectors expressing GDP-D-mannose-4, 6-dehydratase, or to inherently express GDP-D-mannose-4, 6-dehydratase. As a gene for GDP-D-mannose-4, 6-dehydratase, preferably, MUR1 gene derived from *Arabidopsis thaliana* is used.

An expression vector expressing GDP-D-mannose-4, 6-dehydratase can be constructed according to the above method described for an expression vector expressing the protein according to the present invention. However, primers to be used in PCR for cloning DNA encoding GDP-D-mannose-4, 6-dehydratase should be designed by, for example, comparing among the nucleotide sequences of known GDP-D-mannose-4, 6-dehydratase genes. For example, primers having the following nucleotide sequences can be used.

Forward primer:

5'-GTCGAATTCATGGCGTCAGAGAACAAC-3' (SEQ ID NO: 5)

Reverse primer:

5'-GAACTCGAGAGGTTGCTGCTTAGCATC-3' (SEQ ID NO: 6)

An example of the above described transformant with the expression vector expressing GDP-D-mannose-4, 6-dehydratase introduced therein is strain W303/YEp-MUR1-HA (FERM BP-7107). Further, examples of transformants with the expression vector according to the present invention introduced therein include strain W303/YEp-MUR1-HA, pYO-AtFX-Myc (FERM BP-7108).

The above mentioned strain W303/pYO-AtFX-Myc, strain W303/YEp-MUR1-HA, and strain W303/YEp-MUR1-HA,pYO-AtFX-Myc have been deposited with accession Nos. FERM BP-7109, FERM BP-7107, and FERM BP-7108, respectively, at the International Patent Organism Depositary, National Institute of Advanced Industrial Science and Technology (Chuo-6, 1-1-1, Higashi, Tsukuba-shi, Ibaraki, JAPAN).

4. Production of the Protein According to the Present Invention by Culturing the Transformant According to the Present Invention The transformant according to the present invention, that is, a transformant with the expression vector according to the present invention introduced therein (for example, stain W303/pYO-AtFX-Myc), or a transformant with both the former expression vector and an expression vector expressing GDP-D-mannose-4, 6-dehydratase introduced therein, is cultured in an appropriate medium, so that the protein according to the present invention, that is, GDP-4-keto-6-deoxy-D-mannose-3, 5-epimerase-4-reductase can be isolated from the culture.

The transformant according to the present invention can be cultured in a medium by a standard method used for culturing hosts. As media for culturing transformants obtained using microorganisms such as *Escherichia coli* and yeast as hosts, either natural or synthetic media can be used, so far as these media contain sources utilized by microorganisms, such as a carbon source, a nitrogen source, and inorganic salts, and enable efficient culturing of the transform ants.

Examples of carbon sources used herein include carbohydrates such as glucose, fructose, sucrose and starch, organic acids such as acetic acid and propionic acid, and alcohols such as ethanol and propanol.

Examples of nitrogen sources used herein include inorganic acids, such as ammonia, ammonium chloride, ammonium sulfate, ammonium acetate and ammonium phosphate, or ammonium salts of organic acids; other nitrogen-containing compounds; peptone; broth; and corn steep liquor.

Examples of inorganic salts used herein include potassium primary phosphate, potassium secondary phosphate, magnesium phosphate, magnesium sulfate, sodium chloride, ferrous sulfate, manganese sulfate, copper sulfate, and calcium carbonate.

In particular, examples of a medium for culturing yeast include an YPD medium and SD medium.

Transformants obtained using microorganisms as hosts are cultured preferably at 25° C. to 37° C. for 12 hours to 5 days. If necessary, culturing can be performed with aeration, agitation or the like. The pH is not specifically limited, so far as it is in a normally employed range. The pH is kept within a range preferably from 5.0 to 7.5, and more preferably kept at approximately 7.5. The pH is adjusted using inorganic or organic acids, alkaline solutions, or the like. If necessary, antibiotics such as ampicillin or tetracycline may be added to the media while culturing. To culture microorganisms transformed with expression vectors having an inducible promoter as a promoter, inducers may be added to media if necessary.

The media used for culturing transformants obtained using animal cells as hosts include generally used RPMI1640 media, DMEM media, or these media supplemented with fetal calf serum or the like. As media for culturing transformants obtained using plant cells as hosts, generally employed Murashige and Skoog (MS) media are used.

Transformants obtained using animal cells as hosts are cultured, normally, in the presence of 5% $CO_2$, at approximately 37° C. for 1 to 2 days. If necessary, antibiotics, such as kanamycin and penicillin, may be added to the media while culturing.

After culturing, the protein according to the present invention is collected from the culture. When the enzyme is produced within the microorganism or intracellularly, the enzyme can be collected by, for example, disrupting the microorganism or the cell. When the enzyme is produced outside the microorganism or extracellularly, the culture medium is used intact to collect the enzyme, or after the microorganism or the cell is removed by centrifugation or the like, the enzyme can be collected. The enzyme can be collected by one or a combination of standard biochemical methods used for isolation and purification of protein, such as ammonium sulfate precipitation, affinity chromatography, ion exchange chromatography and the like.

Whether the protein obtained as described above is the protein according to the present invention can be confirmed by a standard enzymological reaction, electrophoresis such as SDS polyacrylamide gel electrophoresis, immunological methods such as antigen-antibody reaction, or the like.

5. Production of GDP-L-Fucose

GDP-L-fucose can be produced by culturing the transformant according to the present invention or by enzyme reaction using enzyme sources necessary for production of GDP-L-fucose.

(1) Production of GDP-L fucose by Culturing the Transformant According to the Present Invention A transformant (for example, strain W303/YEp-MUR1-HA, pYO-AtFX-Myc) containing both the expression vector according to the present invention and an expression vector which expresses GDP-D-mannose-4, 6-dehydratase introduced therein is cultured with GDP-D-mannose in an appropriate medium, and then GDP-L-fucose can be isolated and purified from the obtained culture.

Conditions for culturing transformants, such as media, temperature, culturing period, pH and others, are as described in the above "4. Production of the protein according to the present invention by culturing the transformant according to the present invention." If necessary, a cofactor, such as NADPH, may be added to a medium.

GDP-L-fucose can be extracted from the above culture by separating host cells from a medium by centrifugation, disrupting the host cells, followed by another centrifugation. When a host is yeast, for example, cells are disrupted by glass beads and then subjected to centrifugation, so that a supernatant fraction containing GDP-L fucose can be obtained.

GDP-L fucose can be easily isolated and purified from the above supernatant fraction by persons skilled in the art. For example, isolation and purification of GDP-L fucose can be performed by collecting fractions with low molecular weight by a gel filtration technique, and then separating by HPLC. Gel for gel filtration, column size, column eluant, HPLC column and eluant, and the like that are used herein can be appropriately selected by persons skilled in the art.

(2) Production of GDP-L-Fucose by Enzyme Reaction Using Enzyme Sources

GDP-L-fucose can be produced by enzyme reaction using enzyme sources containing necessary enzymes for the production.

When GDP-D-mannose is used as a substrate of an enzyme reaction, required enzymes are GDP-D-mannose-4,6-dehydratase and GDP-4-keto-6-deoxy-D-mannose-3,5-epimerase-4-reductase (the protein according to the present invention). These enzymes may be used herein by culturing in media different transformants which express the two enzymes respectively (for example, strain W303/YEp-MUR1-HA and strain W303/pYO-AtFX-Myc) to separately express the enzymes, and then mixing the enzymes. Preferably, however, a transformant (for example, strain W303/YEp-MUR1-HA, pYO-AtFX-Myc) which expresses both these enzymes is cultured in media for expression. These enzymes can be isolated from the culture of transformants according to a method described in the above "4. Production of the protein according to the present invention by culturing the transformant according to the present invention." Further, the enzyme source used for the above enzyme reaction is not required to be a purified enzyme, and it may be a crude extract, such as the cell extract of the transformant described above.

Enzyme reaction can be performed under appropriate conditions using a reaction solution prepared to contain the above enzyme source and GDP-D-mannose to be used as a substrate. The reaction solution may be supplemented with a cofactor, such as NADPH, if necessary. Reaction conditions are not specifically limited, as the conditions can be appropriately determined by persons skilled in the art. The temperature preferably ranges from 30° C. to 37° C., and more preferably is approximately 37° C. The pH preferably ranges from 6.0 to 8.0, and is more preferably about 7.5. To maintain pH within a desired range, a buffer, such as Tris-HCl, can be used.

GDP-L-fucose can be easily isolated from an enzyme reaction solution by persons skilled in the art. For example, the protein in an enzyme reaction solution is thermally denatured, followed by centrifugation and removal with a membrane filter or the like, and then the GDP-L-fucose is isolated and purified by HPLC.

The GDP-L-fucose is essential as a sugar donor when fucose-containing sugar chains are synthesized. That is, the GDP-L-fucose is useful upon addition of fucose to sugar chains that are thought to be functionally important.

The present invention will be described more specifically below using examples. However, these examples are given only for explanation, and are not intended to limit the technical scope of the present invention.

EXAMPLE 1

Isolation and Sequencing of AtFX Gene

Using the cDNA library of *Arabidopsis* (*Arabidopsis thaliana*), AtFX gene was cloned by the PCR method. QUICK-Clone cDNA (CLONTECH) was used as the cDNA library.

Primers were designed based on the nucleotide sequences submitted to a database (DB name: GenBank; Accession Nos: U38473, U58766 and AF045286). At this time, primers were designed to previously contain KpnI site on the N-terminal portion, and EcoRv site on the C-terminal portion, so that the portion encoding a protein could be easily cleaved by a restriction enzyme, and a gene for labeled antigen or the like could be easily inserted. The nucleotide sequences of the respective primers are as shown below.

Forward primer:

5'-ATT<u>GGTACC</u>ATGTCTGACAAATCTGCCAAAATCTTCGTC-3'

(SEQ ID NO: 3)

Reverse primer:

5'-TTAGTCGAC<u>GATATC</u>TCGGTTGCAAACATTCTTCAAATACCAATCATAAG-3'

(SEQ ID NO: 4)

Here the underlined portion in the nucleotide sequence of the forward primer denotes KpnI site, and that in the nucleotide sequence of the reverse primer denotes EcoRV site. The thus designed primers were synthesized by a standard technique.

PCR was performed using the above QUICK-Clone cDNA (CLONTECH) as a template with the above primers. The composition of the PCR solution is as shown in Table 2 below.

TABLE 2

| Composition of PCR solution | |
|---|---|
| 10 × LA PCR Buffer II (Mg$^{2+}$ plus) | 5 μl |
| dNTP Mixture (2.5 mM each) | 8 μl |
| Forward primer (20 pmol/μl) | 1 μl |
| Reverse primer (20 pmol/μl) | 1 μl |
| cDNA library (1 ng/μl) | 1 μl |
| TaKaRa LA Taq (5 U/μl) | 0.5 μl |
| Water | 33.5 μl |
| Total | 50.0 μl |

PCR was performed by reaction for 30 cycles consisting of the temperature condition of 94° C. for 15 sec (denaturation), 50° C. for 30 sec (annealing) and 68° C. for 2 min (elongation).

The DNA amplification fragment of about 1 kbp obtained by PCR was separated by agarose electrophoresis, and then inserted into pCR2.1 vector using TA cloning kit (Invitrogen). The nucleotide sequence of the cloned DNA was determined by a Sequence Kit (PE Biosystems) using a dideoxy method. The nucleotide sequence and the amino acid sequence encoded by the nucleotide sequence are represented by SEQ ID NO:2 and SEQ ID NO:1, respectively.

EXAMPLE 2

Production of AtFX Gene Expression Vector and MUR1 Gene Expression Vector, and Production of Yeast Transformant Containing These Plasmids 3xMyc gene (Evan et al., Mol. Cell Biol., Vol. 5, 3610 (1985)) encoding a labeled antigen was inserted into EcoRV site in AtFX gene that had been inserted in pCR2.1 vector, in-frame with AtFX gene. AtFX gene containing the Myc gene was cleaved out with KpnI-XhoI. The fragment was inserted into KpnI-SalI site in expression vector YEp352GAP-II which had been prepared by replacing the multicloning site of yeast expression vector YEp352GAP (Roy et al., J. Biol. Chem., Vol. 273, 2583 (1998)) with the EcoRI to SalI portion of the multicloning site of pUC18. Further, a fragment comprising three portions: GAPDH promoter, AtFX-Myc, and GAPDH terminator, was cleaved out using BamHI from the vector. The fragment was inserted into BamHI site in yeast multi-copy vector pY0325 (Qadota et al., Yeast, Vol. 8, 735 (1992)) containing LUE2 marker, thereby constructing AtFX gene expression vector pYO-AtFX-Myc.

MUR1 gene was also cloned by PCR in the manner similar to Example 1 except that PCR primers used herein have the following nucleotide sequences.

Forward primer:

5'-GTCGAATTCATGGCGTCAGAGAACAAC-3' (SEQ ID NO: 5)

Reverse primer:

5'-GAACTCGAGAGGTTGCTGCTTAGCATC-3' (SEQ ID NO: 6)

Next, MUR1 gene was inserted into EcoRI site in YEp352GAP vector (Roy et al., J. Biol. Chem., Vol. 273, 2583 (1998)), and then 3×HA labeled antigen gene was inserted in-frame into PvuII site to construct MUR1 gene expression vector YEp-MUR1-HA.

These expression vectors were separately, or together, transformed into yeast strain W303-1A (ura3, lue2, his3, trp1, ade2) (Kainuma et al., Glycobiology, Vol. 9, 133 (1999) to obtainie strain W303/pYO-AtFX-Myc which contains pYO-AtFX-Myc only, strain W303/YEp-MUR1-HA which contains YEp-MUR1-HA only, and strain W303/YEp-MUR1-HA, pYO-AtFX-Myc which contains both pYO-AtFX-Myc and YEp-MUR1-HA.

EXAMPLE 3

Expression of MUR1 Protein and AtFX Protein Within Yeast

Whether the proteins were expressed in each cell of the transformants obtained in Example 2 was confirmed by Western blotting.

Figure 2:
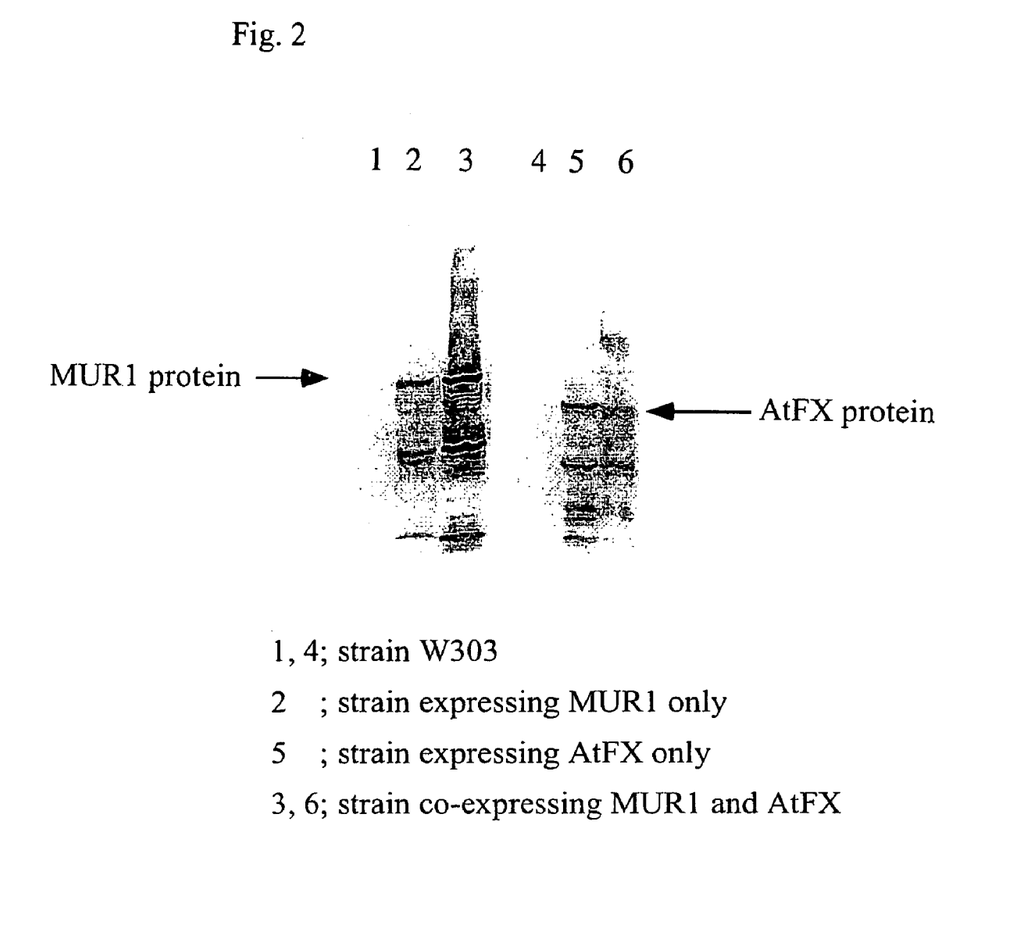
FIG. 2 is a photograph of electrophoresis by western blotting showing expression of MUR1 and AtFX proteins.

First, the above transformants (strain W303/YEp-MUR1-HA, strain W303/pYO-AtFX-Myc, and strain W303/YEp-MUR1-HA, pYO-AtFX-Myc) and strain W303 were separately cultured on SD media at 30° C. for 24 hours, and then the obtained yeast cells were disrupted with glass beads. The disrupted products were centrifuged (100,000×g, 4° C., 60 min) to separate only a cytoplasm fraction, so that only a protein fraction was precipitated using 75% ammonium sulfate. The protein precipitation fraction was dissolved in 20 mM Tris-HCl (pH 7.5) containing 0.5 mM DTT, and desalted with Sephadex G50 (Pharmacia, 20 mM Tris-HCl containing 0.5 mM DTT, pH7.5, 1.3 cm×2.6 cm) to obtaine enzyme solutions. The proteins in the enzyme solutions were determined using BCA kit (RIERCE). The enzyme solutions, each corresponding to 100 μg of protein, were sampled separately, subjected to SDS-PAGE, and electrically transferred to PVDF membranes. Subsequently, expression of each protein was confirmed using HA antibody or Myc antibody (FIG. 2).

As a result, expression of MUR1 protein was confirmed in strain W303/YEp-MUR1-HA and strain W303/YEp-MUR1-HA, pYO-AtFX-Myc; and expression of AtFX protein was confirmed in strain W303/pYO-AtFX-Myc and strain W303/YEp-MUR1-HA, pYO-AtFX-Myc.

EXAMPLE 4

Measurement of GDP-L-Fucose Synthetic Activity

Using GDP-D-mannose as a substrate and 50 mM NADPH as a cofactor, GDP-L-fucose synthetic activity was measured for each enzyme solution prepared in Example 3. First, 50 nmol of GDP-D-mannose was added to 50 μl of a buffer (10 mM Tris-HCl, pH7.5, 10 mM EDTA) containing 50 mM NADPH. Then, the enzyme solutions, each corresponding to 700 μg of the protein, were added to the solution, and then incubated at 37° C. for 1 hour. Next, the reaction solutions were boiled at 100° C. for 3 min, and then the denatured protein precipitated was removed by centrifugation at 10,000 rpm for 5 min. The supernatant with a molecular weight of 10,000 or more was removed using Ultrafree (0.20 μm), and then GDP-L-fucose and GDP-D-mannose were measured by HPLC. HPLC was performed using C18 column (wakosil 5C18–200, Wako Pure Chemical Industries, 0.46 cm in diameter ×25 cm in length) by running 0.5 M $KH_2PO_4$ aqueous solution through the column at 1 ml/min for separation.

Figure 3:
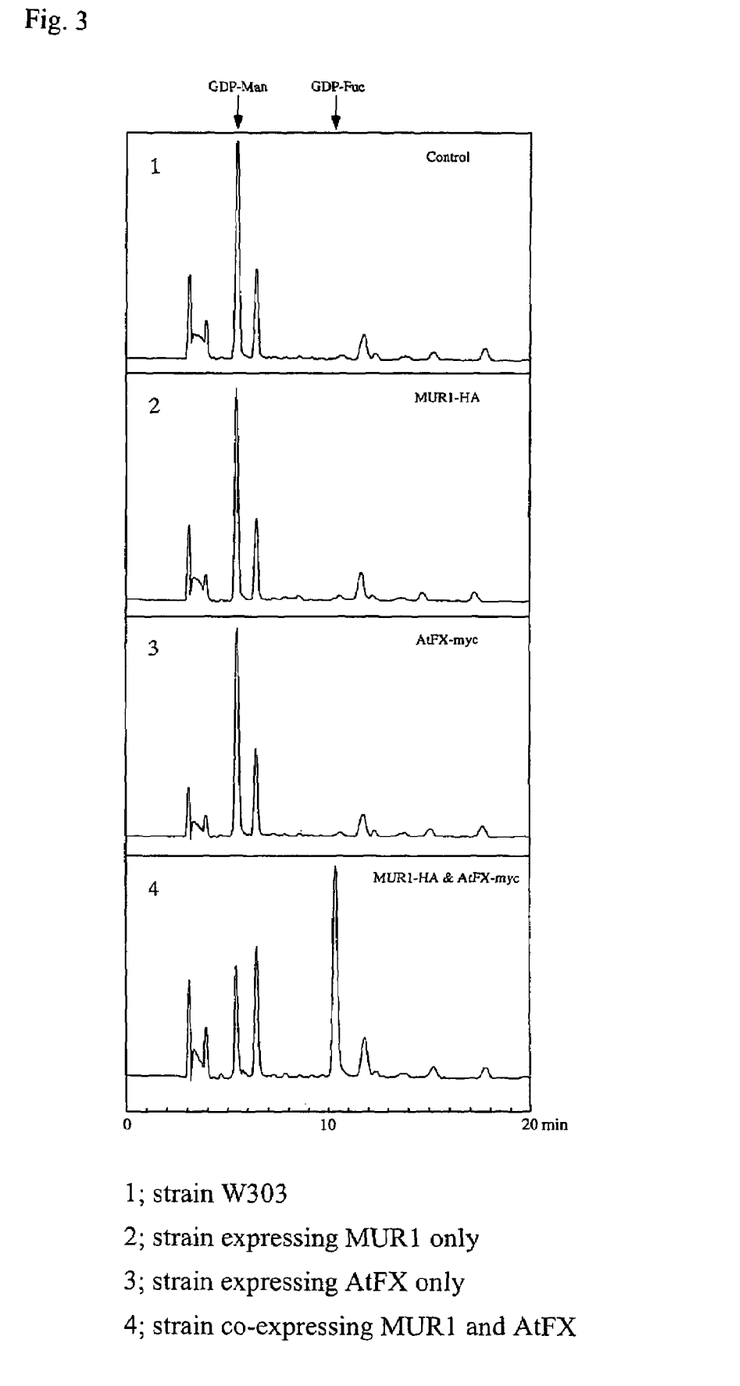
FIG. 3 is a chromatogram by HPLC showing results of measurement of GDP-L-fucose synthetic activity.

As a result, GDP-L-fucose synthetic activity was detected only for strain W303/YEp-MUR1-HA, pYO-AtFX-Myc co-expressing MUR1 protein and AtFX protein (FIG. 3). No activity was shown by the strain expressing MUR1 protein only, suggesting that activity is not maintained for a single expression in yeast. Therefore, when GDP-L-fucose is synthesized, AtFX protein was shown not only to produce GDP-L-fucose after a first reaction step by MUR1 protein, but also to have an action to stabilize the active form of MUR1 protein.

All publications, patents and patent applications cited herein are incorporated herein by reference in their entirety.

INDUSTRIAL APPLICABILITY

The present invention enables efficient mass production of GDP-L fucose which is essential to perform the addition of fucose, which has a very important function in sugar chains. At present, a technique to uniformly synthesize the sugar chain of glycoprotein has not been established. A possible technique is to synthesize uniform sugar chains by modifying in vitro sugar chains, and for which a sugar nucleotide is essential as a sugar donor. In particular, GDP-L-fucose is prohibitively expensive among fucose, and therefore it is impractical to perform in vitro modification reaction in large quantities. However, if the present invention enables the supply of GDP-L-fucose in large quantities, high-performance sugar chains with fucose added thereto can be synthesized in vitro.

The invention claimed is:

1. An isolated DNA comprising the nucleotide sequence SEQ ID NO: 2.

2. An expression vector which comprises the DNA of claim 1.

3. An isolated host cell transformed with the expression vector of claim 2.

4. A process for producing GDP-4-keto-6-deoxy-D-mannose-3, 5-epimerase-4-reductase, which comprises culturing the transformant of claim 3 in a medium and collecting GDP-4-keto-6-deoxy-D-mannose-3, 5-epimerase-4-reductase from the obtained culture.

5. An isolated host cell transformed with: (a) the expression vector of claim 2; and (b) an expression vector comprising DNA encoding GDP-D-mannose-4, 6-dehydratase produced by strain W303/YEp-MUR1-HA (FERM BP-7107).

6. A process for converting GDP-mannose into GDP-L-fucose using the transformant of claim 5.

7. A process for producing GDP-L-fucose which comprises culturing the transformant of claim 5 together with GDP-D-mannose in a medium, and collecting GDP-L-fucose from the obtained culture.

8. The transformant of claim 5, the transformant being strain W303/YEp-MUR1-HA, pYO-AtFX-Mye (FERM BP-7108).

* * * * *